US007659110B2

(12) United States Patent
Kudoh et al.

(10) Patent No.: US 7,659,110 B2
(45) Date of Patent: Feb. 9, 2010

(54) DNA AMPLIFICATION DEVICE

(75) Inventors: Seiichi Kudoh, Nagano (JP); Ryoji Kobayashi, Nagano (JP)

(73) Assignee: Thermogen Inc., Nagano (JP)

(*) Notice: Subject to any disclaimer, the term of this patent is extended or adjusted under 35 U.S.C. 154(b) by 1131 days.

(21) Appl. No.: 11/151,435

(22) Filed: Jun. 14, 2005

(65) Prior Publication Data

US 2006/0166226 A1 Jul. 27, 2006

(30) Foreign Application Priority Data

Jan. 21, 2005 (JP) ............................ 2005-013773

(51) Int. Cl.
*C12M 1/00* (2006.01)
*C12M 3/00* (2006.01)

(52) U.S. Cl. .................................................. 435/303.1

(58) Field of Classification Search ............... 435/303.1
See application file for complete search history.

(56) References Cited

U.S. PATENT DOCUMENTS 6,489,111 B1 * 12/2002 Takahashi et al. .............. 435/6
6,706,519 B1 * 3/2004 Kellogg et al. ........... 435/287.2
7,192,557 B2 * 3/2007 Wu et al. ...................... 422/81
2003/0190608 A1 * 10/2003 Blackburn ..................... 435/6
2004/0043479 A1 * 3/2004 Briscoe et al. ........... 435/288.5
2004/0072334 A1 * 4/2004 Benett et al. ............. 435/286.1
2004/0248146 A2 * 12/2004 Atwood et al. ................. 435/6
2005/0009101 A1 * 1/2005 Blackburn .................. 435/7.1
2005/0084957 A1 * 4/2005 Atwood et al. ........... 435/304.1
2006/0239862 A1 * 10/2006 Nakajima et al. ........... 422/100

FOREIGN PATENT DOCUMENTS

JP 2003-174863 A 6/2003

* cited by examiner

*Primary Examiner*—Walter D Griffin
*Assistant Examiner*—Lydia Edwards
(74) *Attorney, Agent, or Firm*—Birch, Stewart, Kolasch & Birch, LLP

(57) ABSTRACT

A processing block 2 is composed of a base 5, where an upper substrate 6 formed with a metal material M and a lower substrate 7 formed with the metal material M or a ceramic material E are adhered, and cells C . . . supported by this base 5; and the cells C . . . are secured to the upper substrate 6 and/or the lower substrate 7 at least via cell positioners 6*s* . . . established in the upper substrate 6 for positioning the cells C . . . , respectively.

At the same time, at least the thickness Ld of regions Xc . . . situated under the cells C . . . in the lower substrate 7 is selected to be 1.0 [mm] or thinner, and, a thermo-module(s) comes into contact with the lower surface of the base 5.

19 Claims, 8 Drawing Sheets

DNA AMPLIFICATION DEVICE

BACKGROUND OF THE INVENTION

1. Field of the Invention

The present invention relates to a DNA amplification device suitable for use when amplifying DNA (deoxyribonucleic acid).

2. Description of the Relevant Art

In general, the PCR method (polymerase chain reaction method) is known as a method for DNA amplification. The PCR method is a method where primers, an enzyme(s) and deoxyribonucleoside triphosphate, reacted with a DNA sample, are added to the DNA sample, whereupon the reaction solution is heated (or cooled down) by a heat cycle changed according to a pre-determined temperature pattern, and concurrently, where the sequential repetition of the heat cycle results in the amplification of the DNA.

Another DNA amplification device for realizing the PCR method is also known, for example, in the publication of Japanese Laid-Open Patent Application No. 2003-174863, which discloses a DNA amplification device equipped with a heating & cooling means established on an inorganic substrate, multiple reaction cells formed in a lattice pattern on the heating & cooling means, on the upper surfaces of which reaction cells is established a temperature measuring means, where electric heat conversion devices, in which a P-type peltiert element and an N-type peltiert element are regarded as one pair, are used as a heating & cooling means, and concurrently, where they are arranged in a lattice pattern at positions opposing the reaction cells.

For the cells (reaction cells) established in the DNA amplification device, multiple concave parts are normally formed & arranged at pre-determined intervals on the upper surface of a block board using a silicone wafer material or an aluminum material, the concave parts being directly constructed as cells (reaction cells), or in a construction in which the cells (tubes) are filled into the concave parts. With such construction, the block board where the cell group is formed functions as a processing block, with the bottom surface of the block board being heated or cooled down from the heating & cooling side of a thermo-module 3.

In the meantime, the heating & cooling means (thermo-module) where the peltiert elements are used is normally configured as shown in FIG. 15. The thermo-module 3 shown in the diagram is constructed with a structure where multiple peltiert elements d . . . are connected [with each other] and regarded as a series aggregate P, the series aggregate P being interposed between a pair of substrates 51 & 52. In this case, multiple electrodes e . . . are established at a constant interval on the facing surfaces (internal surfaces) of each of the substrates 51 & 52, the end of each peltiert element d . . . generally being joined to each electrode e . . . using solder. With this construction, if the electrification direction to the series aggregate P is switched to the forward direction or reverse direction, the thermo-module 3 can be operated for heating or for cooling. At this time, during heating, the heat radiation side (opposite the heating & cooling side) of the thermo-module 3 is cooled down. At the same time, when cooling, the heat radiation side of the thermo-module 3 is heated, so an aluminum heat sink 53 is attached to the heat radiation side, heat radiation (or heat absorption) being performed via the heat sink 53.

However, in the case of using a processing block provided with this cell group for the DNA amplification device, there are problems that the following nonconformities may occur:

In this type of DNA amplification device, for pre-determined heating & cooling performance to a reaction solution, prompt temperature-rising performance or temperature-fall performance is especially required. However, this DNA amplification device cannot sufficiently respond to this required performance. In the DNA amplification device, as shown in FIG. 14, heating is performed according to a heat cycle where, after heating is performed at 94 [° C.] for T1 [sec], separate heating is performed at 50 [° C.] for T2 [sec], and heating is additionally performed at 72 [° C.] for T3 [sec]. At the same time, the heat cycle is normally repeated dozens of times. In this case, in a temperature pattern F shown in the chart, a temperature-falling period of time Td and temperature-rising periods of time Tf and Ts, in addition, another temperature-fall period of time Th to lower the temperature from 94 [° C.] to 4 [° C.] when storing a reaction solution within the cells at a low temperature must be as short as possible. Because the block board, where the heat capacity and the coefficient of thermal expansion are great, and which lowers thermal conductivity, intervenes between the cells and the thermo-module 3, prompt temperature-rising & temperature-falling controls cannot be realized. Without prompt temperature-rising & temperature-falling controls, there is not only no realization of flexible and accurate temperature control, but also in the longer duration in one process, it will lead the reduction of process efficiency and the reduction of power saving properties.

Further, the repetitive operation of the heat cycle may cause creeping at the soldered joints between the electrodes e . . . and the peltiert elements d . . . due to the modulus of longitudinal elasticity, the coefficient of the thermal expansion and a difference in thermal expansion, depending upon the temperature in the substrates 51 & 52, the electrodes e . . . and the peltiert elements d . . . , which creeping causes a thermal stress fraction, such as poor contact or breaking of wire, to the soldered joints. In particular, the generated direction of creeping is opposite between the heat radiation side (the substrate 52 side) and the heating & cooling side (the substrate 51 side). In other words, as shown by the outline arrows in FIG. 15, when creep is generated in the contraction direction on either the heat radiation side or the heating & cooling side, since separate creeping will be generated in the expansion direction on the other side, the thermal stress will also be substantially doubled.

In the meantime, in order to inhibit the generation of creeping, it is effective to reduce the temperature variation at the soldered joints as much as possible. For this purpose, it is necessary to enlarge the volume of the heat sink 53 and to reduce the thermal resistance. However, there is a limit to enlargement of the volume of the heat sink 53. Normally, the thickness of a foundation 53*b* of the heat sink 53 is established at 10-15 [mm] from the viewpoint of reducing the thermal resistance and enhancing the rigidity, at the same time, preventing a warp (curvature) of the foundation 53*b*. Even in this case, the temperature variation of the soldered joints is approximately 5-10 [° C.], and the temperature variation at the soldered joints cannot be sufficiently inhibited, and the At the same time, it causes great enlargement of the entire thermo-module 3. In addition, in the case that the multiple thermo-modules 3 are scattered and arranged, the temperature greatly varies between each thermo-module 3, so even DND amplification to all cells cannot be performed.

SUMMARY OF THE INVENTION

The objective of the present invention is to provide a DNA amplification device that enables the prompt temperature-rising and temperature-falling controls, and that realizes the flexible and accurate temperature control, where the reduction of the duration in one process enables the improvement of the process efficiency and the power saving properties.

Another objective of the present invention is to provide a DNA amplification device where excellent thermal responsiveness is secured and the temperature variation on the heat radiation side of the thermo-modules is reduced, and where the reduction of the stress added to the peltiert elements comprising the thermo-module prevents thermal stress fracture at the thermo-module(s), enhancing durability (life expectancy).

Another objective of the present invention is to provide a DNA amplification device where the high quality of a processing block that has cells which can contain a reaction solution including a DNA sample, can be easily realized, and where the accuracy and stability of physical effects can be secured.

Another objective of the present invention is to provide a DNA amplification device where the uniform heat distribution enables the reducing variation of temperatures between each cell, and where the variance or shift of positions upon assembly or operation of each cell can be reduced.

In order to accomplish these objectives, the present invention is characterized by the fact that, in a DNA amplification device equipped with a processing block provided with cells that can contain a reaction solution including a DNA sample, a thermo-module(s) using peltiert elements for heating and cooling the processing block, and a controller that controls the electrification at least to the thermo-module(s); the processing block is comprised of a base constructed by adhering an upper substrate formed with a metal material and a lower substrate formed with a metal material or a ceramic material, and the cells supported by this base, the cells being secured to the upper substrate and/or the lower substrate via at least cell positioners established in the upper substrate for positioning the cells. At the same time, at least the thickness of regions situated under the cells in the lower substrate is selected to be 1.0 [mm] or thinner, and, the thermo-module(s) comes into contact with the lower surface of the base.

Further, the present invention is characterized by the fact that the processing block is comprised of a substrate formed with a metal material and the cells supported by the substrate; the cell positioners formed with a cylinder burling, where the protrusion upward from a pre-determined position results in fitting into the lower side of an outer circumferential surface of the cell, respectively, are established; the cells are fitted into the cell positioners, and respectively secured, with the thermo-module(s) coming into contact with the lower surface of the substrate. At the same time, slits for warp absorption, which are situated cross-wise to an end edge of the substrate, and are formed with a pre-determined length, are established along the end edge at a pre-determined intervals in the end edge.

In addition, the present invention is characterized by the fact that the processing block is comprised of a substrate formed with a metal material and the cells supported by the substrate; the cell positioners formed with a cylinder burling, where the protrusion upward from a pre-determined position results in fitting into the lower side of an outer circumferential surface of the cell, respectively, are established, with the cells being fitted into the cell positioners, and respectively secured, the thermo-module(s) coming into contact with the lower surface of the substrate. At the same time, a retainer plate that has control holes engaged or joined with the upper side of each cell, and corresponding to the position of each cell, respectively, is established.

BRIEF DESCRIPTION OF THE DRAWING

FIG. 4 (*b*) is an assembly explanatory diagram that includes a partial cross sectional construction of the processing block;

FIG. 7 (*b*) is an assembly explanatory diagram that includes the cross sectional construction of the processing block;

FIG. 8 (*b*) is an assembly explanatory diagram that includes the cross sectional construction of the processing block;

DETAILED DESCRIPTION OF THE PREFERRED EMBODIMENTS

Preferred embodiments relating to the present invention are described hereafter, with reference to the drawings. The present invention is not limited to the attached drawings which are provided for easily understanding the present invention. Further, detailed descriptions of the well-known portions are omitted in order to avoid ambiguity.

Figure 1:
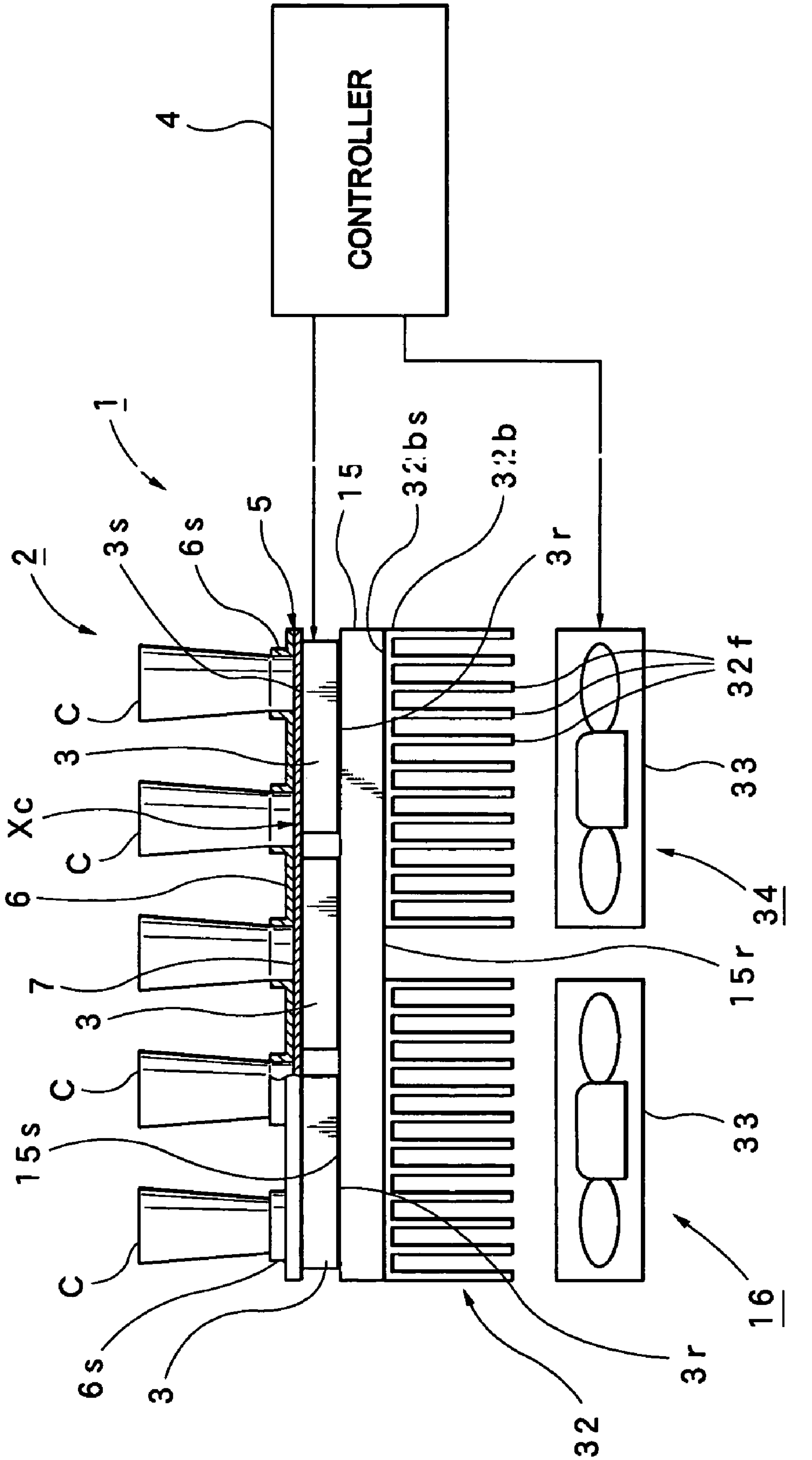
FIG. 1 is a schematic diagram of a DNA amplification device relating to the best embodiment of the present invention.
Figure 2:
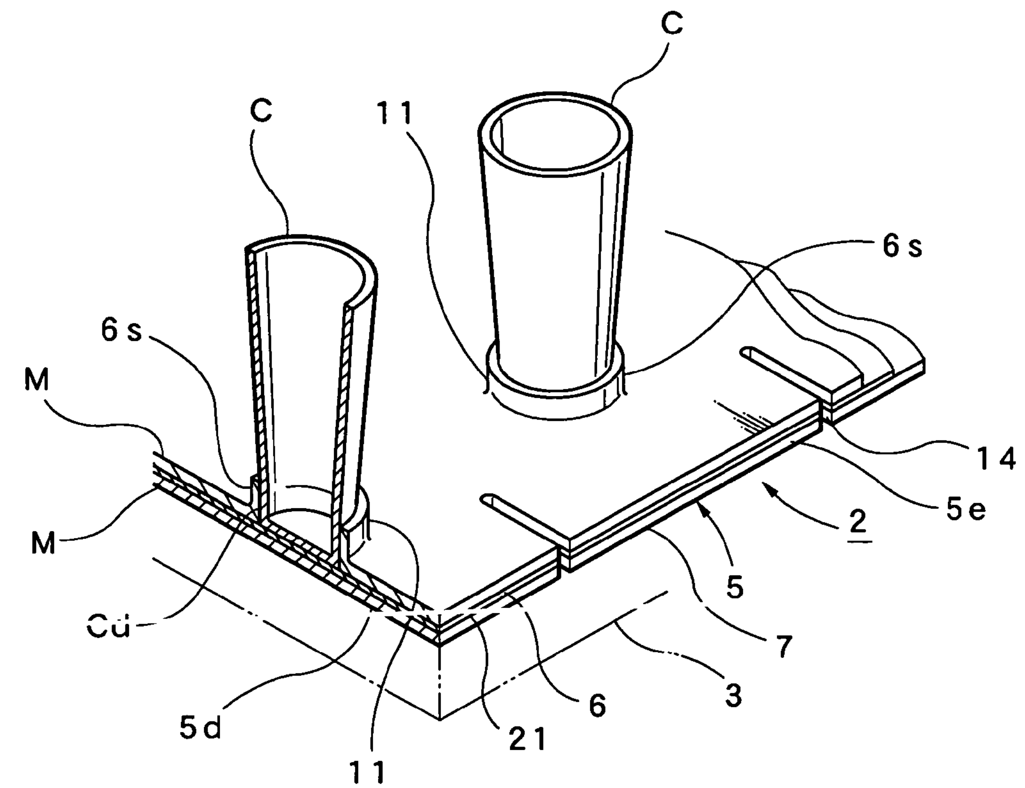
FIG. 2 is a partially cross-sectional perspective view that shows a processing block in the DNA amplification device.
Figure 3:
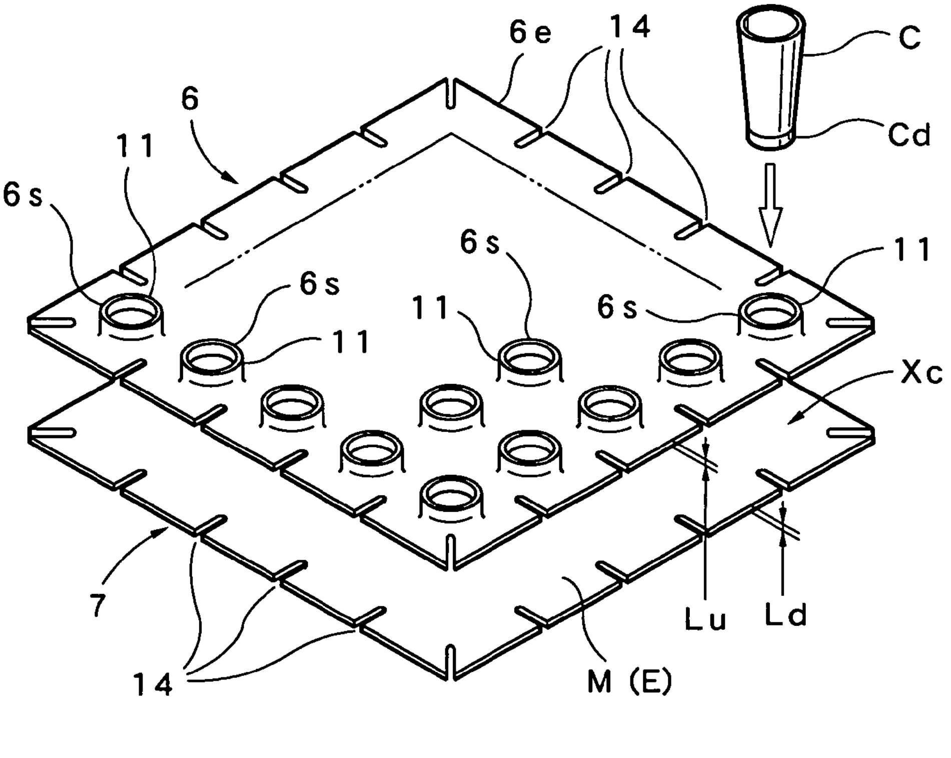
FIG. 3 is an exploded perspective view that partially shows the processing block in the DNA amplification device.

First, the construction of a DNA amplification device 1 relating to the present invention is described hereafter with reference to FIG. 1 through FIG. 3.

Figure 15:
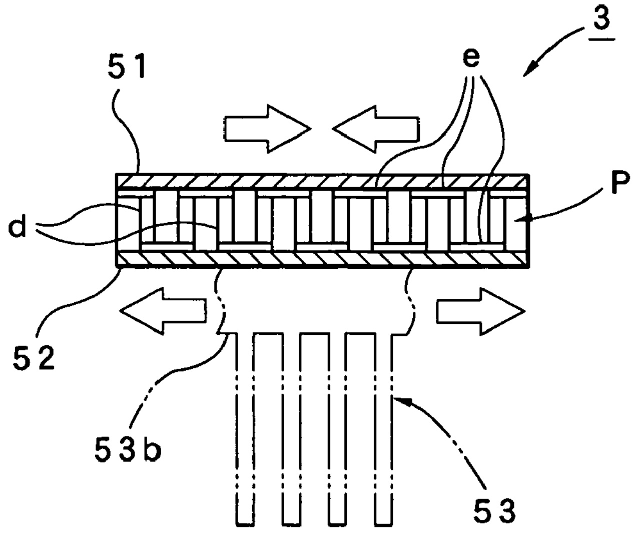
FIG. 15 PRIOR ART

In FIG. 1, the symbol 3 . . . indicates one, two or more thermo-modules. Each thermo-module 3 . . . is the basically the same as the above-mentioned thermo-module 3 shown in FIG. 15. In other words, the thermo-module 3 is constructed with a structure in which multiple peltiert elements d . . . are connected [with each other] and are regarded as the series aggregate P, and this series aggregate P is interposed by a pair of the substrates 51 & 52. The multiple electrodes e . . . are established at a constant interval on the facing surfaces (the internal surfaces) of each of the substrates 51 & 52, and the end of each peltiert element d . . . is generally joined with each electrode e . . . using solder. With such construction, if the electrification direction to the series aggregate P is switched to the forward direction or reverse direction, the thermo-module 3 can be operated for heating or for cooling.

In the meantime, a surface 15*s* of a heat radiation copper board 15 comes into contact with a surface at the heat radiation side 3*r* in each thermo-module 3 . . . In this case, thermal conduction grease is interposed between the surface at the heat radiation side 3*r* . . . in the thermo-module 3 . . . and one surface 15*s* of the heat radiation copper board 15, and each thermo-module 3 . . . and the heat radiation copper board 15 are secured using a fixture, such as a screw.

The entire heat radiation copper board 15 is integrally formed with a copper material, and act the same time, it is formed to be a plate with a uniform thickness. In this case, the thickness of the heat radiation copper board 15 is 4 [mm] or thicker, preferably selected to be within the range of 5-8 [mm]. Furthermore, in the case that the thickness is less than 4 [mm], the thermal diffusivity and the heat capacity become insufficient.

Further, a surface at the opposite side from the one surface 15*s* of the heat radiation copper board 15 is a heat radiation surface 15*r*, in which is installed and one, two or more heat sinks 32. [Each] heat sink 32 . . . has a foundation 32*b* that has an adherence surface 32*bs* . . . adhered to the heat radiation surface 15*r*, and many heat radiation fins 32*f* . . . that protrude vertically from a surface, which is opposite to this adherence surface 32*b* . . . , and a whole is integrally formed with an aluminum material. In this case, for the thickness of the foundation 32*b* . . . , approximately 2-3 [mm] of thickness that can maintain the heat radiation fins 32*f* . . . is sufficient. The thickness of the foundation 53*b* in the above-mentioned general heat sink 53 is normally established to be approximately 10-15 [mm] from the viewpoints of reducing the thermal resistance, enhancing rigidity and preventing warpage (curvature) of the foundation 53*b*. However, in the present embodiment, the heat radiation copper board 15 functions for reducing the thermal resistance, enhancing the rigidity. At the same time, preventing a warp of the foundation 32*b* . . . for the thickness of the foundation 32*b* in the heat sink 32 . . . , approximately 2-3 [mm] of thickness is sufficient as mentioned above.

One, two or more blast fans 33 . . . are arranged opposing each heat sink 32. enabling air-cooling of each heat sink 32 . . . by [each] blast fan 33 . . . , and this heat sink 32 . . . and the blast fan 33 . . . comprise an air-cooling device 34 (cooling means 16), respectively. In addition, the symbol 4 indicates a controller, and each blast fan 33 . . . and each of the above-mentioned thermo-module(s) 3 . . . are connected to this controller 4, respectively. With this connection, the controller 4 performs an electrification control to the thermo-module(s) 3 . . . . At the same time, performs the operation control to the blast fan(s) 33 . . .

On the other hand, a processing block 2 is installed to the surface(s) on the heating & cooling side 3*s* . . . in the thermo-module(s) 3, resulting in a structure where the thermo-module 3 . . . is interposed between the heat radiation copper board 15 (the heat sink 32 . . . ), arranged at the lower side, and the processing block 2, which in turn is arranged on the upper side, as shown in FIG. 1.

The processing block 2 is a major component of the present embodiment, and is equipped with a base 5, constructed by adhering an upper substrate 6 and a lower substrate 7 formed with a metal material M, respectively, and cells C supported by the base 5. In this case, the entire upper substrate 6 is formed to be rectangular with a thin plate material made from a copper material (such as, oxygen free copper) selected to be 0.2 [mm] of thickness Lu as shown in FIG. 3. At the same time, multiple cell positioners 6*s* . . . are arranged on the surface of the upper substrate 6. Furthermore, the number of the illustrated cell positioners 6*s* . . . is 5×5, or a total of 25. It is desirable that the thickness Lu of the upper substrate 6 be 0.2 [mm]. However, as long as it is within the range of 0.1-0.5 [mm], a sufficient effect can be obtained. One cell positioner 6*s* (this applied to other cell positioners 6*s* . . . ) is formed with a cylinder burling 11, which protrudes upward from a pre-determined position of the upper substrate 6, fitted (press-fitted) into the lower side of the outer circumference Cd of the below-mentioned cell C. The formation of the cell positioner 6*s* with the cylinder burling 11 contributes to simplifying the manufacture of the entire processing block 2.

In the meantime, the entire lower substrate 7 is formed to be rectangular with a thin plate material formed with a copper material (such as, oxygen free copper) in a thickness of 0.2 [mm] Ld, as shown in FIG. 3. It is desirable that the thickness Ld of the lower substrate 7 be 0.2 [mm]. However, similar to the upper substrate 6, as long as it is within the range of 0.1-0.5 [mm], a sufficient effect can be obtained. Therefore, at least the thickness Ld of regions Xc . . . , situated under the cells C . . . in the lower substrate 7, becomes 0.2 [mm], respectively. Then, the lower substrate 7 is adhered to the lower surface of the upper substrate 6. In this case, for the adhesion between the upper substrate 6 and the lower substrate 7, blazing material 21 obtained primarily from a silver material is used and these are joined. As the blazing material 21, a blazing material for vacuum blazing, such as JIS (Japanese Industrial Standards) Z3261 that contains 78 [%] of silver and 22 [%] of copper, can be used. Owing to the use of the blazing material 21, the physical characteristics (thermal conductivity and the coefficient of thermal expansion) of the blazing material 21 itself becomes substantially the same as that of the upper substrate 6 and the lower substrate 7, as a result of which a strong joint can be realized. At the same time, it also becomes stronger in withstanding the stress from the repetition of temperature variations by the peltiert elements (thermo-module(s) 3 . . . ). An actual range of repetitive temperature variation is within the range of 4-100 [° C.], and any expansion difference by the thermal expansion can be ignored. If the copper material formed to be 0.2 [mm] (0.1-0.5 [mm]) of thickness is used for the upper substrate 6 and the lower substrate 7, press molding generally of a thin plate with a high thermal conductivity enables the easy obtainment of the upper substrate 6 and the lower substrate 7.

In addition, slits 14 . . . for warp absorption, formed crosswise to the end edge 5*e* from the end edge 5*e*, and formed with a pre-determined length, are established in the base 5 along the end edge 5*e* at pre-determined intervals. In this case, the width of the [each] slit 14 is selected to be 0.1 [mm] or thicker, and the length is selected to be approximately 5-15 [%] of the length of one side of the end edge 5*e*. At the same time, the slits 14 are situated in between each of the cell positioners 6*s* . . . , respectively. Furthermore, the slits 14 . . . , as shown in FIG. 3, can be formed to be the same positions both in the upper substrate 6 and the lower substrate 7 when manufactured, or they can be formed not in manufacturing the upper substrate 6 and the lower substrate 7, but after the adhesion of the upper substrate 6 and the lower substrate 7.

Each slit 14 . . . functions as follows:

In the heating mode, the lower substrate 7, which makes contact with the thermo-module(s) 3 . . . , is heated, with the heat being conducted to the below-mentioned cells C . . . . On this occasion, the heat is radiated from the external surface of the cells C . . . and the upper substrate 6 to the air outside, slightly lowering the surface temperature of the heat radiation region is slightly lowered, with potential deformation to warp the end edge from the upper substrate 6 upward. However, normally, since the upper surface of the upper substrate 6 is pressed onto the thermo-module(s) 3 by a heat-insulating material, such as rubber or resin, [coating] the outside of the cells C . . . , deformation occurs expanding toward the plane direction of the upper substrate 6. The establishment of the slits 14 . . . results in the absorption of the deformation expanding toward the plane. At the same time, there is an effect to reduce the temperature difference between the center region of the base 5 and the end edge 5*e* side. In the case of not establishing the slits 14 . . . , the temperature difference between the center region of the base 5 and the end edge 5*e* side is approximately 3-4 [° C.]. However, this has been improved to 1-1.5 [° C.] in the case of establishing the slits 14 . . . Consequently, establishing the slits 14 . . . enables the effective absorption of warp which may occur to the base 5 associated with the temperature variation upon operation, the securing of the accuracy and stability of the physical effects in the processing block 2, and the additional contribution to the improvement of durability.

In the meantime, as shown in FIG. 2 and FIG. 3, the cells C are formed to be in a cup-like state having approximately 0.2-1.5 [ml] of volume where a reaction solution including a DNA sample is containable, respectively. These cells C can be squeeze-molded by press-working a thin plate material (approximately 0.2-0.3 [mm] of thickness) formed with a copper material (such as oxygen free copper) with comparatively high thermal conductivity. Then, when securing the cells C to the base 5, the lower sides Cd of the outer circumferential surfaces of the cells C are press-fitted into the cylinder positioners 6*s* and respectively secured. Furthermore, the lower surfaces of the bottom surfaces Cb can be blazed onto the upper surface of the lower substrate 7 along with the upper substrate 6. In this case, the lower sides Cd of the outer circumferential surfaces and the cell positioners 6 do not have to be always press-fitted, but may be just fit in.

Furthermore, when installing the processing block 2 onto the surface(s) on the heating & cooling side 3*s* in the thermo-module(s) 3 . . . , the thermal conductive grease intervenes between the lower surface of the base 5 and the surface at the heating & cooling side 3*s* in the thermo-module(s) 3 . . . , and each thermo-module 3 . . . and the base 5 are secured using a fixture, such as a screw.

In processing block 2 endowed with the above construction, the heat capacity in the processing block 2 itself and an effect of the coefficient of thermal expansion on deformation, such as a warp, can be reduced, enhancing thermal conductivity, making it possible to promptly control temperature-rising and temperature-falling, realizing flexible and accurate temperature control can be realized, enabling a reduction of duration in one process with the improvement of the process efficiency and the power saving properties. Further, since the excellent thermal responsiveness at the processing block 2 results in reduction of the temperature variation at the heat radiation side of the thermo-module(s) 3 . . . , the thermal stress fracture at the thermo-module(s) 3 . . . can be prevented, and the durability (life expectancy) can be enhanced. Further, the stress added to the peltiert elements d . . . comprising the thermo-module(s) 3 . . . can be reduced, with improved durability. In addition, if the base 5 is constructed by adhering the upper substrate 6 and the lower substrate 7 formed with the metal material M, and at least the thickness Ld of the regions XC . . . situated under the cells C . . . in the lower substrate 7 is formed to be 0.1-0.5 [mm]. At the same time, the cells C . . . are secured to the upper substrate 6 and/or the lower substrate 7, enabling the obtainment of processing block 2 with high quality.

Processing block 2 can also be modified and used as follows:

In the above-mentioned embodiment, the lower substrate 7 is formed using a copper material. However, it can also be formed using a ceramic material E. For the ceramic material E, alumina ($Al_2O_3$), alumina nitride (AlN, silicon nitride ($Si_3N_4$) generally are utilized, and the thickness Ld is selected to be 0.3-1.0 [mm] (preferably, 0.6-0.7 [mm]). Further, for the adhesion to the upper substrate 6, a silicon material-base adhesive, which excels in the thermal conductivity, can be used. Furthermore, in the case of forming the lower substrate 7 using the ceramic material E, the above-mentioned slits 14 . . . become unnecessary.

Even though using this ceramic material E [for the lower substrate 7] causes a slight slow-down in the promptness of the temperature control because its thermal conductivity is smaller than that of the copper material, there are advantages such that the deformation of the upper substrate 6 due to the expansion (or contraction) upon the temperature-rising or temperature-tailing can be better prevented, and the uniformity of the temperature at each cell C . . . can be enhanced. At the same time, the improvement of following properties relating to the deformation of the upper substrate 6 results in it becoming difficult [for the lower substrate 7] to be exfoliated from the upper substrate 6.

In addition, it is also possible to construct the processing block 2 without using the lower substrate 7. In this case, since the lower substrate 7 is not used, only the upper substrate (substrate) 6 shown in FIG. 3 is used, and it is constructed such that the thermo-module(s) 3 . . . directly comes into contact with the lower surface of substrate 6. Further, the point where the slits 14 . . . for warp absorption, which are situated cross-wise to the end edge 6*e* . . . of the substrate 6, formed with a pre-determined length, are established along the edge end 6*e* at a pre-determined interval in the edge end of the substrate 6, and another point where the cell positioners 6*s* . . . formed from a cylinder burling 11, where the protrusion upward from a pre-determined position of the substrate 6 results in fitting into the lower side Cd . . . of the outer circumferential surface of the cell C . . . , respectively, are the same as those of the above-mentioned upper substrate 6 shown in FIG. 1 and FIG. 2. Then, the cells C . . . can be secured by press-fitting the cells C . . . into the cell positioners 6*s* . . . , respectively. On this occasion, it is also possible to supplementarily use a securement means, such as blazing, as the occasion demands.

Even though using only the substrate 6 causes a slight reduction in the stability of a partial thermal contact with the thermo-module(s) 3 . . . , the heat capacity in the processing block 2 can be reduced. At the same time, the thermal conductivity can be additionally enhanced, with the advantage that more prompt (faster) temperature-rising control and temperature-falling control can be realized.

How to use the DNA amplification device 1 relating to the present embodiment and its operation are explained hereafter, with reference to FIG. 1 through FIG. 3 and FIG. 14.

Figure 14:
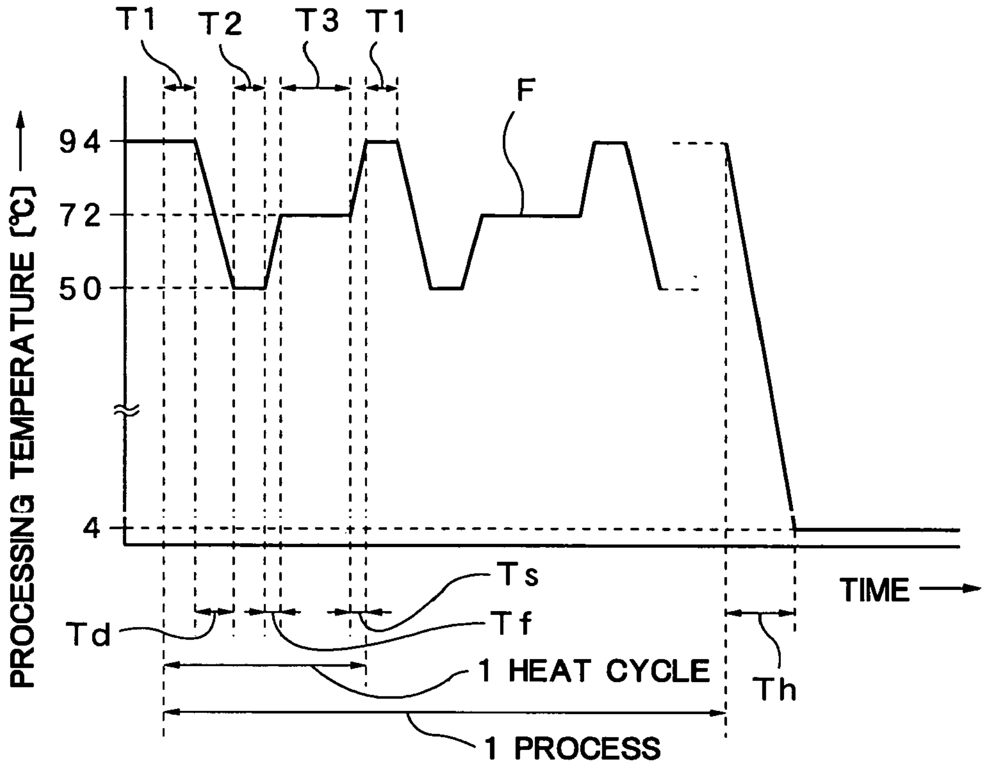
FIG. 14 PRIOR ART
FIG. 14 is a characteristic chart for period of time vs. processing temperature when operating a DNA amplification device; and, FIG. 15 is a pattern schematic view of the thermo-module in a DNA amplification device.

First, the controller 4 is provided with a sequence control function for the purpose of controlling the electrification of the thermo-modules 3 . . . in order to obtain the temperature pattern F shown in FIG. 14. In this case, the processing temperature shown in the temperature pattern F is the internal temperature of the cells C . . . Therefore, although the illustration is omitted, one, two or more temperature sensors are mounted to pre-determined positions in the processing block 2, and a feedback control to the processing temperature is performed. On this occasion, the internal temperature of the cells C . . . can be generally estimated according to the database obtained from preliminary experiment(s).

Further, the controller 4 controls the blast fan(s) 33 . . . to be the operation mode. Furthermore, as the occasion demands, the blast fan(s) 33 . . . can be controlled using an inverter.

In the meantime, a reaction solution where primer, an enzyme(s) and deoxyribonucleoside triphosphate, which are reacted with a DNA sample, are respectively added to the DNA sample, is contained within the cells C . . . . Then, in the controller 4, first, electrification-controls the thermo-module(s) 3 . . . , and heating is performed at 94 [° C.] for T1 [sec] (for example, 15 [sec]), causing the dissociation of the DNA with a double helix structure. Next, the thermo-module (s) 3 . . . are electrification-controlled, and are cooled down to 50 [° C.]. At the same time, once the temperature reaches 50 [° C.], it is maintained at 50 [° C.] for T2 [sec] (for example, 15 [sec]). This causes the binding of the primers to a specific region of the DNA (annealing). Next, the thermo-module(s) 3 . . . is electrification-controlled, and heated to 72 [° C.]. At the same time, once the temperature reaches 72 [° C.], it is maintained at 72 [° C.] for T3 [sec] (for example, 30 [sec]). These operations result in the synthesis of a complementary strand to a specific gene bound with the primers by the enzyme. The above-mentioned operations are regarded as a single heat cycle, the repetition of which dozens of times (for example, 30 times) enables amplification processing of the DNA. On the other hand, when the DNA amplifying processing is finished, as shown in FIG. 14, cooling (pull-down) is performed from 94 [° C.] to 4 [° C.]. Once the temperature reaches 4 [° C.], control is performed to maintain the temperature, enabling the storage of the amplified DNA at a low temperature.

In this case, during the heating operation, the processing block 2 is heated by the heating & cooling side 3*s* of the thermo-module 3, and the heat radiation side 3*r* is cooled down. At the same time, during the cooling operation, the processing block 2 is cooled down by the heating & cooling side 3*s* of the thermo-module 3, and, the heat radiation side 3*r* is heated. The quantity of heat on the heat radiation side 3*r* is radiated via a heat radiation copper board 15, the quantity of heat radiation becoming the sum of the quantity of heat deprived from the processing block 2 and the quantity of heat based on the input electric power for the cooling effect produced by the thermo-module(s) 3 itself. Although the heating & cooling capability (heating & cooling speed) is also greatly affected by the heat radiation on the heat radiation side 3*r*, the excellent thermal diffusivity and great heat capacity by the heat radiation copper board 15 enables controlling temperature variation at the soldered joints between the peltiert elements d . . . in the thermo-module(s) 3 . . . and the electrodes [e . . . ] to be approximately 3 [° C.] or less. Therefore, the thermal stress fraction, such as poor contact or breaking of wire, at the soldered joints occurring due to thermal stress (creep) can be prevented, and the durability (life expectancy) of the thermo-module(s) 3 . . . can be dramatically enhanced.

Further, according to the DNA amplification device 1 relating to the present embodiment, excellent heat radiation by the heat radiation copper board 15 results in the discharge from the heat radiation side 3*r* in a thermo-module 3 filled with heat. At the same time, in addition, the structure of the processing block 2 enables the enhancement of the heating performance and the cooling performance, as a result of which the temperature-falling period Td and the temperature-rising periods Tf and Ts in FIG. 14 are shortened, and prompt temperature-rising and temperature-falling performance can be realized. In particular, after amplification processing is finished, it is desirable that the temperature-falling period Th (FIG. 14) from 94 [° C.] to 4 [° C.] when shifting to the storage mode become as short as possible, making it possible to shorten the temperature-falling period of Th because of the excellent heat radiation by the heat radiation copper board 15. Therefore, shortening the duration in an entire DNA amplification process can be accomplished. At the same time, it can also contribute to the saving power property; in addition, it can also contribute to the miniaturization of the thermo-module(s) 3 . . .

In addition, even in the case of scattering and arranging multiple thermo-modules 3 . . . , because the variation of the temperature between each thermo-module 3 . . . is reduced, uniform DNA amplification in all of the cells C . . . can be realized.

A modified embodiment of the processing block 2 and cooling means 16 is explained hereafter, with reference to FIG. 4 through FIG. 13.

Figure 4:
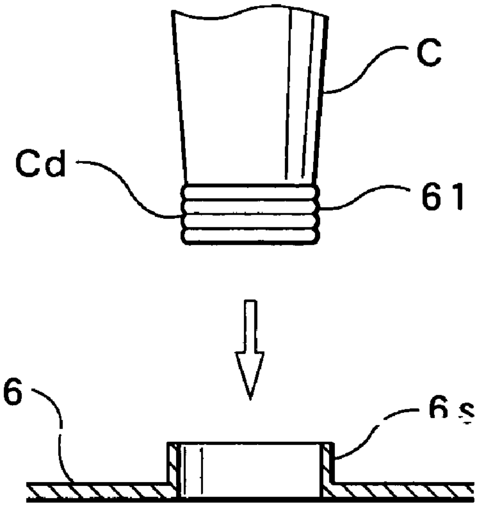
FIG. 4 (*a*) is an assembly explanatory diagram that includes a partial cross sectional construction of the processing block relating to a modified embodiment of the DNA amplification device.
Figure 4:
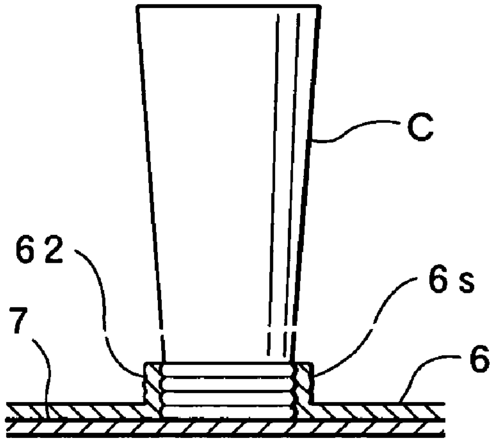

FIGS. 4 (*a*) and (*b*) show a modified embodiment of the processing block 2. The processing block 2 shown in FIGS. 4 (*a*) and (*b*) is designed so that after the lower side Cd of the outer circumferential surface of the cell C is inserted (or press-fitted) into the cell positioner 6*s*, a caulking processing to the outer circumference of the cell positioner 6*s* results in the establishment of a chalk 62 and the they are respectively secured, as shown in FIG. 4 (*b*). This enables certain prevention of omission of the cells C from the cell positioners 6*s*, respectively, and also enables strong securing of the cells C to the upper substrate 6. Consequently, as shown in FIG. 4 (*a*), it is desirable that asperities 61 are respectively pre-established on the lower side Cd of the outer circumferential surface of the cell C. Furthermore, in FIGS. 4 (*a*) and (*b*), any components which are the same as those in FIG. 1 through FIG. 3, are marked the same, so their configurations are clarified.

Figure 5:
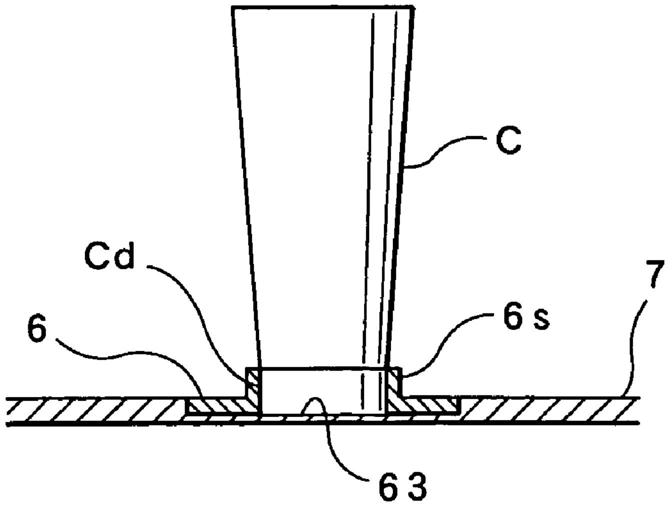
FIG. 5 is a cross sectional schematic view of the partial processing block relating to another modified embodiment in the DNA amplification device.
Figure 6:
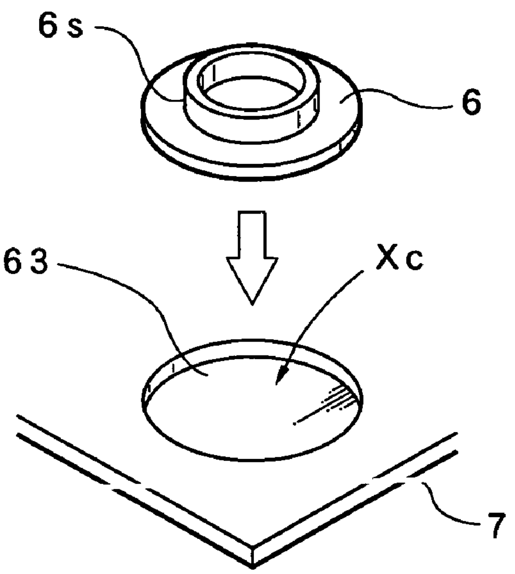
FIG. 6 is an exploded perspective view that partially shows the processing block shown in FIG. 5.

FIG. 5 and FIG. 6 show a modified embodiment of the upper substrate 6 and the lower substrate 7. In the present modified embodiment, the donut ring plate-state upper substrate 6 is integrally formed on the lower ends of the cell positioners 6*s*, and housing concave parts 63 where the upper substrate 6 is fitted are formed on the lower substrate 7. As shown in FIG. 5, the upper substrate 6 is fitted into the insides of the housing concave 63, which are secured using blazing. Therefore, the thickness of the lower substrate 7 is established to be 0.4 [mm], which is the thickness where the upper substrate 6 and the lower substrate 7 are piled, as shown in FIG. 1 through FIG. 3, and the thickness of the region where the housing concavity 63 is formed on the lower substrate 7 can be selected to be 0.2 [mm]. Furthermore, in FIG. 5 and FIG. 6, any components which are the same as those in FIG. 1 through FIG. 3, are marked the same, so their configurations are clarified.

Figure 7:
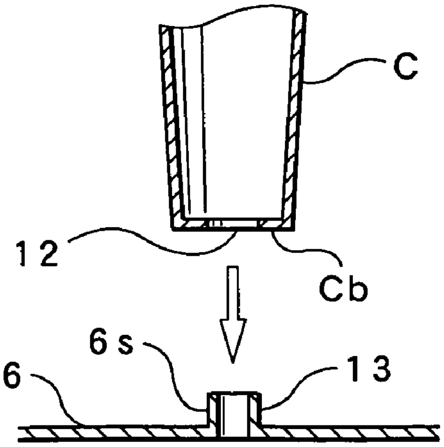
FIG. 7 (*a*) is an assembly explanatory diagram that includes the cross sectional construction of the processing block relating to another modified embodiment in the DNA amplification device.
Figure 7:
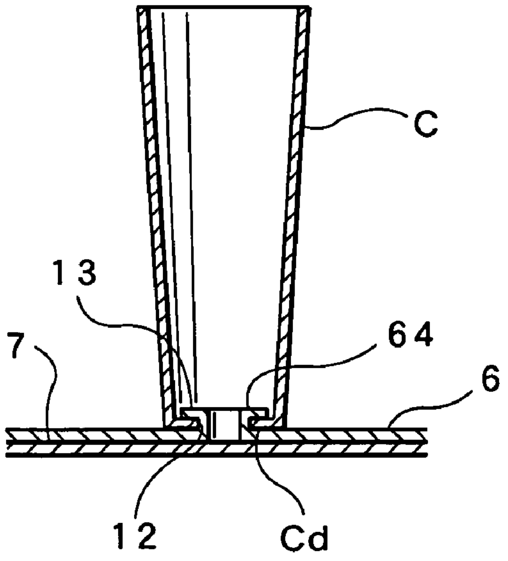

FIGS. 7 (*a*) and (*b*) show the cell positioner 6*s* formed with the cylinder burling 13, which protrudes upward from the pre-determined position of the upper substrate 6, and which is inserted into a hole 12 perforated in the bottom surface Cb of the cell C. Consequently, as shown in FIG. 7 (*a*), the hole 12 is perforated in the bottom surface Cb of the cell C in advance. When assembly, the burling 13 is inserted into the hole 12 from the lower side, and pressure from the inside of the cell C to the burling 13 is applied from the upper end side, as shown in FIG. 7 (*b*), the caulking processing for expanding the burling 13 outward results in the establishment of the caulk 64, resulting in the interposition of the bottom surface Cb of the cell C by the caulk 64 and they are secured. With this construction, since the lower substrate 7 itself becomes a substantial bottom surface of the cell C, additional reduction of heat capacity and the improvement of the thermal conductivity in the processing block 2 can be realized. Furthermore, in FIGS. 7 (*a*) and (*b*), components which are the same as those in FIG. 1 through FIG. 3, are marked the same, so their construction are clarified.

Figure 8:
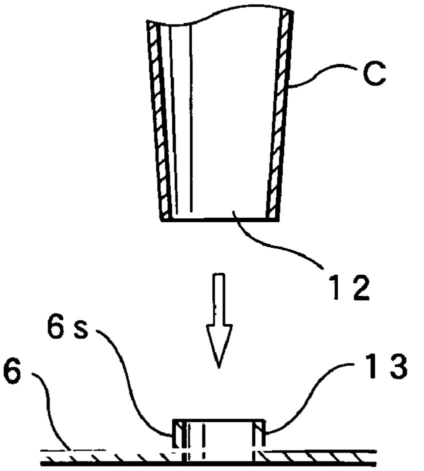
FIG. 8 (*a*) is an assembly explanatory diagram that includes the cross sectional construction of the processing block relating to another modified embodiment in the DNA amplification device.
Figure 8:
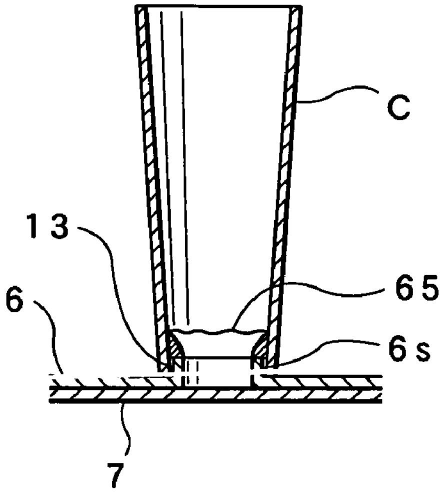

FIGS. 8 (*a*) and (*b*) show another securement means to secure the cell positioner 6*s* and the cell C shown in FIGS. 7 (*a*) and (*b*). Even in the case of FIGS. 8 (*a*) and (*b*), as with FIGS. 7 (*a*) and (*b*), the cell positioner 6*s* is formed with the cylinder burling 13 that protrudes upward from the pre-determined position of the upper substrate 6, and that is inserted into the hole 12 perforated in the bottom surface Cb of the cell C. With this construction, as shown in FIG. 8 (*b*), the burling assembly 13 is inserted into the hole 12 from the lower side, and the end of the burling 13 and the internal circumferential surface of the cell C are secured using the blazing 65 from the inside of the cell C. Therefore, it is desirable that the hole 12, as shown in FIG. 8 (*a*), be established throughout the entire bottom surface Cb of the cell C.

Figure 9:
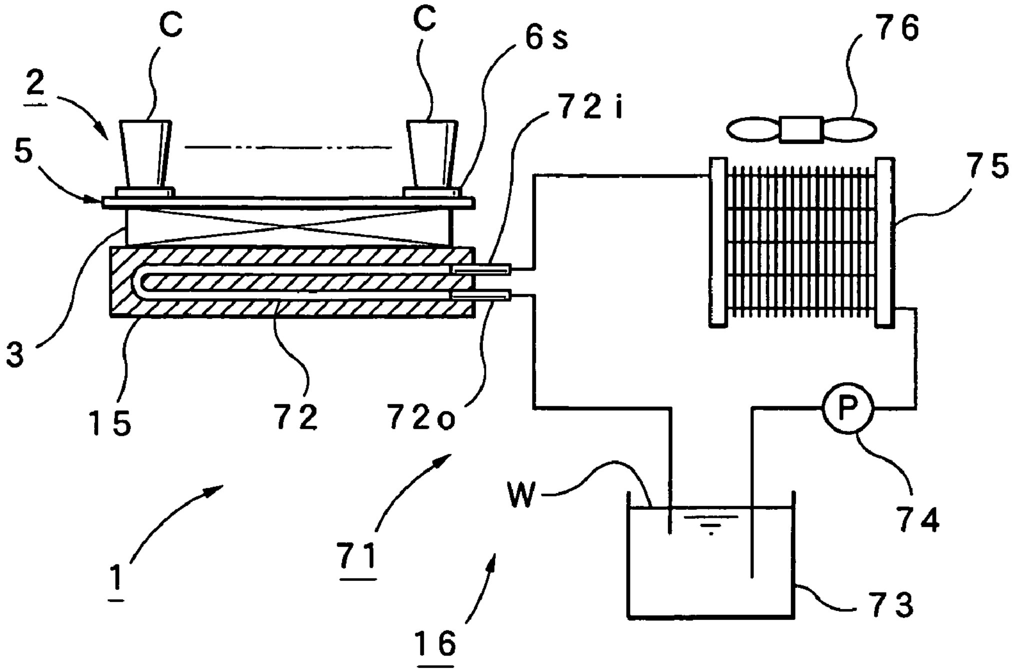
FIG. 9 is a schematic view of a cooling means relating to a modified embodiment in the DNA amplification device.
Figure 10:
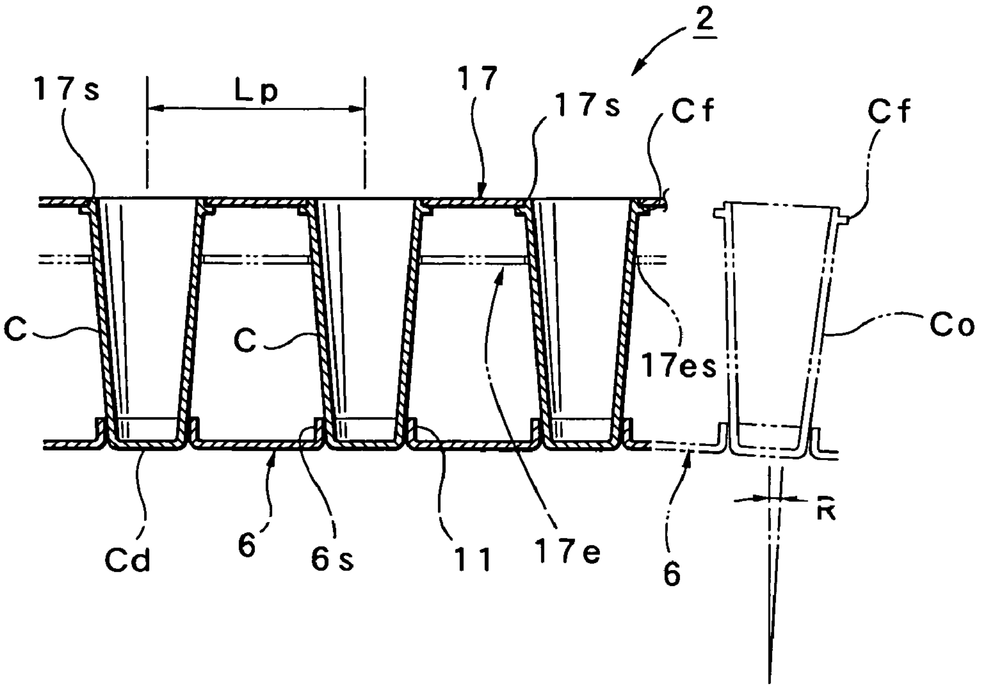
FIG. 10 is a cross-sectional schematic view of a processing block relating to another modified embodiment in the DNA amplification device.
Figure 11:
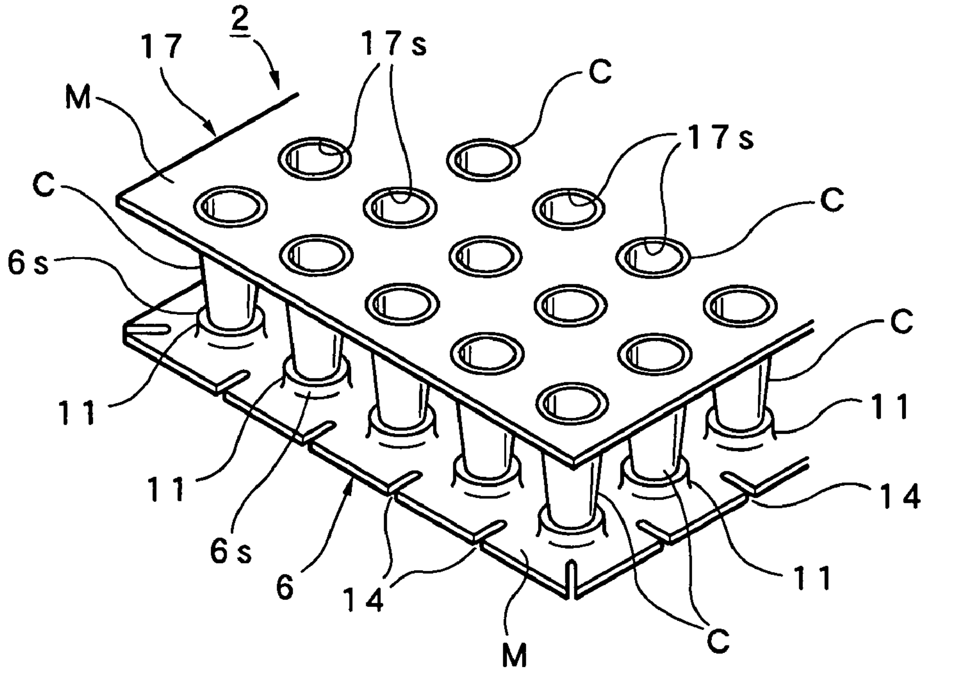
FIG. 11 is a perspective view of the processing block.

FIG. 9 shows a modified embodiment of the cooling means 16. The cooling means 16 shown in FIG. 9 is composed of a cooling device 71 that cools down by circulating a cooling liquid W within the heat radiation copper board 15. In other words, a liquid pathway (jacket) 72 for circulating the cooling liquid W is formed inside the heat radiation copper board 15, and is further is equipped with a cooling liquid tank 73 to store the cooling liquid W, a solution sending pump 74, a radiator (thermal converter) 75 and a blast fan 76 outside. With this construction, the cooling liquid W stored in the cooling liquid tank 73 is supplied to the radiator 75 by the solution sending pump 74, and after air cooling is performed by radiator 75, the cooling liquid W is supplied to the inflow entrance 72*i* of the liquid pathway 72. Then, cooling liquid W that has flowed into the liquid pathway 72, and where the heat exchange has been performed, is discharged from a water outlet 72*o* of the liquid pathway 72 and returns to the cooling liquid tank 73. With the cooling device 71 shown in FIG. 9, since the inside of the heat radiation copper board 15 is forceably cooled down due to the cooling liquid W, comparatively high cooling performance can be secured. Furthermore, FIG. 9 shows a case in which the radiator 75 is cooled down (air cooled) by the blast fan 76, but the radiator 75 can be generally cooled down by a thermo-module generally similar to the thermo-module 3 shown in FIG. 15. Other than that, in FIG. 9, any components which are the same as those in FIG. 1 are marked the same, and its construction is clarified. At the same time, a detailed explanation is omitted.

FIG. 10 through FIG. 13 show that the processing block 2 is composed of substrate 6 formed with the metal material M and the cells C supported by this substrate 6, and the cell positioners 6*s* formed with the cylinder burling 11 . . . , where the protrusion upward from a pre-determined position results in the fitting into the lower side Cd of the outer circumferential surface of the cell C, respectively, are established in the substrate 6, and the cells C are fitted into these cell positioners 6*s* and are respectively secured. In addition, a retainer plate 17 is established which is provided with control holes 17*s* engaged or joined with the upper portion of each cell C . . . , and corresponding to the position of each cell C. Therefore, the thermo-module(s) 3 . . . respectively come into contact with the lower surface of the substrate 6.

Figure 12:
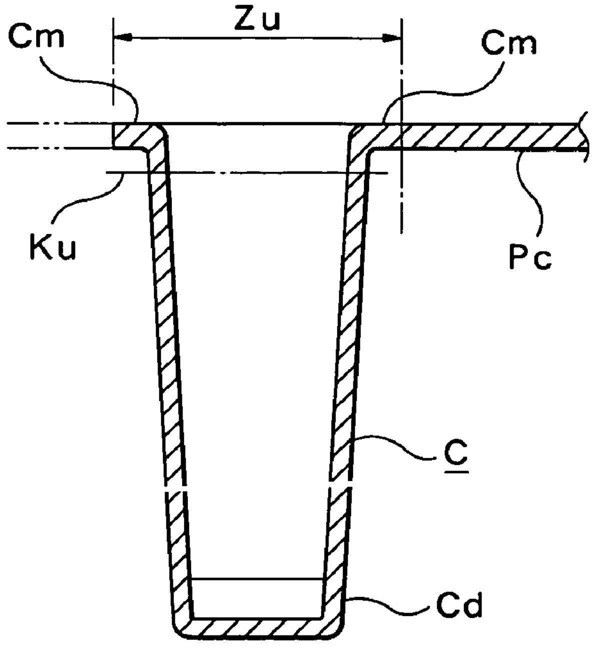
FIG. 12 is an explanatory view of one process when molding a cell of the processing block.
Figure 13:
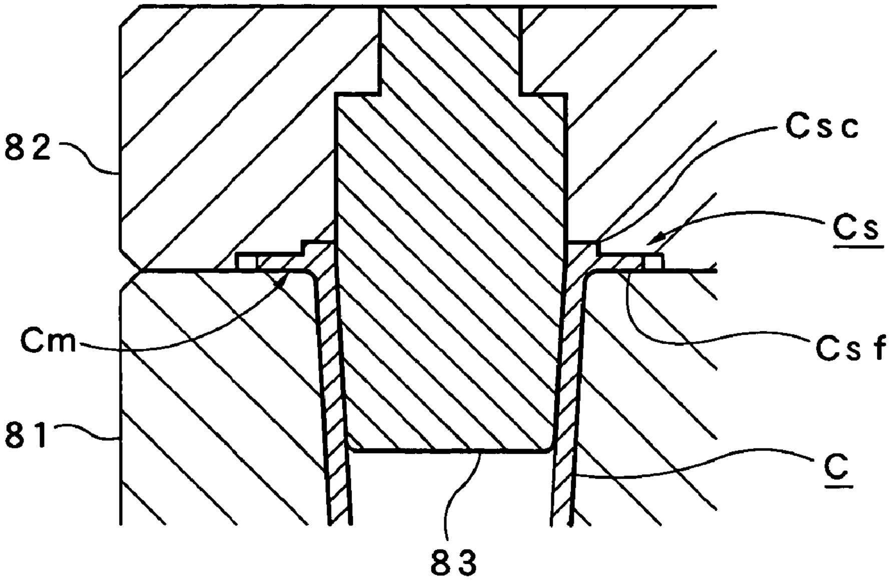
FIG. 13 is an explanatory view of another process when molding a cell of the processing block.

In this case, for the substrate 6 and the retainer plate 17, a copper material with 0.1-0.5 [mm] of thickness, preferably 0.3 [mm], is used, respectively. Further, the control holes 17*s* . . . in the retainer plate 17 are respectively formed from a hole where the upper end of the cell C . . . is fitted. Furthermore, on the outer circumferential surface of the illustrated cell C, a ring-state flange Csf that protrudes outward at a position slightly lower from the top end of the cell C, and for this flange Csf, as shown in FIG. 12, after the cell C is squeeze-molded by press-working a thin plate material Pc using a copper material, a mark Cm generated when cutting. Normally, the cell C shown in FIG. 2, as shown in FIG. 12, is cut within the range indicated with the symbol Zu for the purpose of the preventing deformation of the cell C after squeeze-molding the cell C. After cutting, it is cut with the line indicated with the symbol Ku. However, in the present modified invention, as shown in FIG. 13, re-press working to the mark Cm by utilizing a lower mold 81, an upper mold 82 and a core mold 83 results in the establishment of a position retainer Cs comprised of a cylinder Csc, which protrudes upward from the above-mentioned flange Csf and the upper edge of this flange Csf, and which is fitted into the control hole 17*s*. Since this results in the fitting of the upper end of the cell C into the control hole 17*s*, the cell C is accurately positioned to the retainer plate 17. In this case, the retainer plate 17 and each cell C . . . can be seized by press-fitting, or these can generally be joined by a blazing material. In addition, for the processing block 2 in the present modified embodiment, only the substrate 6 is used. In other words, the lower substrate 7 in the embodiment shown in FIG. 3 is not used, but the same construction where only the upper substrate 6 shown in the diagram is used is applied. Therefore, the above-mentioned slits 14 . . . for warp absorption are established on the substrate 6.

According to the present modified embodiment, since it has construction that the substrate 6 supports each cell C . . . and the thermo-module(s) 3 . . . comes into contact with the lower surface of this substrate 6, even though the stability of a partial thermal contact to the thermo-module(s) 3 . . . is slightly lowered, the heat capacity in the processing block 2 can be reduced. At the same time, thermal conductivity can be additionally enhanced, and prompter (faster) temperature-rising control or temperature-falling control can be realized.

Further, since the retainer plate 17 is established, warp of the substrate 6 can be prevented. In other words, when the temperature is high (90 [° C.] or higher), the cells C positioned at the outer edge side of the substrate 6 lean [outward] relative to the cell(s) C situated in the center by an angle R as a cell Co shown with a virtual line in FIG. 12. This happens because even if the temperature of the center side of the substrate 6 is increased, the temperature on the outer edge side of the substrate 6 is decreased due to heat radiation, so warp is generated on the substrate 6. In order to absorb the warp, the above-mentioned slits 14 . . . are established for warp absorption. However, it is difficult to perfectly absorb the warp. Since the retainer plate 17 controls the upper end position of each cell C, the existence of this retainer plate 17 prevents warping of the substrate 6.

Furthermore, the case where the illustrated retainer plate 17 is fitted into the upper end of [each] cell C . . . has been shown, and it can be designed such that the retainer plate 17 is seized on the outer circumferential surfaces in the middle of the vertical direction of the cells C . . . , as [another] retainer plate 17*e* shown with the virtual line in FIG. 12. In this case, control holes 17*es* . . . , [whose size] is equivalent to the outer diameter of the outer circumferential surface in the intermediate position, respectively, are established. At the same time, when assembly, after each cell C is dropped into each control hole 17*es* . . . of the retainer plate 17, the position (height) is adjusted by making contact between the upper end of each cell C . . . and one flat plane, and then, each cell C . . . can be mounted onto each cell positioner 6*s* . . . of the substrate 6. Even in this case, the retainer plate 17*e* and each cell C . . . can be generally seized by press-fitting, and can be joined by blazing. Therefore, in the present modified embodiment, to engage or join the retainer plate 17 with the upper side of each cell C . . . means to engage or join the retainer plate 17 at the position upward from the substrate 6.

Therefore, according to the present modified embodiment, since there is a connection between each cell C with the retainer plate 17, the variation of the temperature between each cell C. can be reduced due to the uniformalization of heat dissemination. At the same time, the variation and fluctuation of the position of each cell C . . . upon the assembly or operation can be reduced. Therefore, the reduction of a pitch Lp in between each cell C . . . shown in FIG. 12 as much as possible enables the reduction of the variation of the temperature. Other than that, in FIG. 10 through FIG. 13, components which are the same as those in FIG. 1 through FIG. 3, are marked the same, so their construction is clarified. At the same time, the detailed explanation is omitted.

As described above, the embodiments have been explained in detail. However, the present invention is not limited to these embodiments, but the construction of the details and the methods generally can be optionally modified within the scope of the concept of the present invention. At the same time, addition and deletion are also applicable as the circumstances demand. For example, as the metal material M, a copper material is most preferable. However, this does not exclude the utilization of other metal materials M, such as aluminum. Further, the DNA amplification device 1 in the present invention includes an enzyme reaction device, as well. In addition, in FIG. 1 through FIG. 11, various embodiments relating to the partial construction or component construction have been provided. However, it is possible that these can appropriately be combined as usage and be implemented.

What is claimed is:

1. A DNA amplification device, wherein, in a DNA amplification device equipped with a processing block, which has cells that can contain a reaction solution including a DNA sample, respectively, a thermo-module(s) using peltiert elements for heating and cooling the processing block, and a controller that controls the electrification at least to the thermo-module(s), wherein the processing block is comprised of a base, which is constructed by adhering an upper substrate formed with a metal material and a lower substrate formed with a metal material or a ceramic material, and the cells supported by this base; and the cells are secured to the upper substrate and/or the lower substrate via at least cell positioners established in the upper substrate for positioning the cells, and at the same time, at least the thickness of the regions situated under the cells in the lower substrate is selected to be 1.0 [mm] or thinner, and, the thermo-module(s) comes into contact with the lower surface of the base.

2. The DNA amplification device according to claim 1, wherein, for the upper substrate, a copper material formed to have 0.1-0.5 [mm] [of thickness] is used.

3. The DNA amplification device according to claim 1, wherein, in the lower substrate, a copper material formed to have 0.1-0.5 [mm] [of thickness] is used at least for the regions situated under the cells.

4. The DNA amplification device according to claim 1, wherein, in the lower substrate, a ceramic material formed to have 0.1-0.5 [mm] [of thickness] is used at least for the regions situated under the cells.

5. The DNA amplification device according to claim 1, wherein, the cell positioners are formed with a cylinder burling that protrudes upward from a pre-determined position of the upper substrate, and that is fitted into the lower side of the outer circumferential surface of the cell, respectively.

6. The DNA amplification device according to claim 1, wherein, the cell positioners are formed with a cylinder burling that protrudes upward from a pre-determined position of the upper substrate, and that is inserted into a hole perforated in the bottom surface of the cell, respectively.

7. The DNA amplification device according to claim 1, wherein, slits for warp absorption, which are situated in a cross direction from an end edge relative to the end edge, and which are formed with a pre-determined length, are established along the end edge at a pre-determined interval in the upper substrate and/or the lower substrate formed with a metal substrate, respectively.

8. The DNA amplification device according to claim 1, wherein, the DNA amplification device is equipped with a heat radiation copper board, which comes into contact with the heat radiation side of the thermo-module(s), and which is formed with a copper material whose thickness is selected to be 4 [mm] or thicker, and a cooling means to cool down the heat radiation copper board.

9. The DNA amplification device, wherein, in a DNA amplification device equipped with a processing block, which has cells that can contain a reaction solution including a DNA sample, respectively, a thermo-module(s) using peltiert elements for heating and cooling the processing block, and a controller that controls the electrification at least to the thermo-module(s), the processing block is comprised of a substrate formed with a metal material and cells supported by the substrate; cell positioners formed with a cylinder burling where the protrusion upward from a pre-determined position results in fitting into the lower side of an outer circumferential surface of the cell, respectively, are established; the cells are fitted into the cell positioners, and they are secured, respectively; and, the thermo-module(s) comes into contact with the lower surface of the substrate, and at the same time, slits for warp absorption, which are situated in crossing direction to an end edge of the substrate, and which are formed with a pre-determined length, are established along the end edge at a pre-determined interval in the end edge.

10. The DNA amplification device according to claim 9, wherein, for the substrate, a copper material formed to have 0.1-0.5 [mm] [of thickness] is used.

11. The DNA amplification device according to claim 9, wherein, the cell positioners are formed with a cylinder burling that protrudes upward from a pre-determined position of the substrate, and that is fitted into the lower side of the outer circumferential surface of the cell, respectively.

12. The DNA amplification device according to claim 9, wherein, the cell positioners are formed with a cylinder burling that protrudes upward from a pre-determined position of the substrate, and that is inserted into a hole perforated in the bottom surface of the cell, respectively.

13. The DNA amplification device, wherein, in a DNA amplification device equipped with a processing block, which has cells that can contain a reaction solution including a DNA sample, respectively, a thermo-module(s) using peltiert elements for heating and cooling the processing block, and a controller that controls the electrification at least to the thermo-module(s), the processing block is comprised of a substrate formed with a metal material and cells supported by the substrate; cell positioners formed with a cylinder burling, where the protrusion upward from a pre-determined position results in fitting into the lower side of an outer circumferential surface of the cell, respectively, are established; the cells are fitted into the cell positioners, and they are secured, respectively; and, the thermo-module(s) comes into contact with the lower surface of the substrate; at the same time, a retainer plate that has control holes engaged or joined with the upper side of each cell, and corresponding to the position of each cell, respectively, are established.

14. The DNA amplification device according to claim 13, wherein, for the upper substrate, a copper material formed to have 0.1-0.5 [mm] [of thickness] is used.

15. The DNA amplification device according to claim 13, wherein, for the retainer plate, a copper material formed to have 0.1-0.5 [mm] [of thickness] is used.

16. The DNA amplification device according to claim 13, wherein, the cell positioners are formed with a cylinder burling that protrudes upward from a pre-determined position of the upper substrate, and that is fitted into the lower side of the outer circumferential surface of the cell, respectively.

17. The DNA amplification device according to claim 13, wherein, the cell positioners are formed with a cylinder burling that protrudes upward from a pre-determined position of the upper substrate, and that is inserted into a hole perforated in the bottom surface of the cell, respectively.

18. The DNA amplification device according to claim 13, wherein, slits for warp absorption, which are situated in a crossing direction from an end edge relative to the end edge, and which are formed with a pre-determined length, are established along with the end edge at a pre-determined interval in the substrate formed with a metal material.

19. The DNA amplification device according to claim 13, wherein, position retainers that have cylinders and flanges, which fit into the control holes by re-press working a mark generated when squeeze-molding and cutting the cells using press-working a thin plate material, are established at the upper end of the cells, respectively.

* * * * *